(12) United States Patent
Lehrman et al.

(10) Patent No.: US 8,574,145 B2
(45) Date of Patent: Nov. 5, 2013

(54) SYSTEM AND METHOD FOR TRAINING AND PROMOTING A CONDITIONED REFLEX INTERVENTION DURING SLEEP

(75) Inventors: Michael L. Lehrman, Washington, DC (US); Michael D. Halleck, Frederick, CO (US)

(73) Assignee: Sleep Methods, Inc., Bethesda, MD (US)

( * ) Notice: Subject to any disclaimer, the term of this patent is extended or adjusted under 35 U.S.C. 154(b) by 397 days.

(21) Appl. No.: 12/881,982

(22) Filed: Sep. 14, 2010

(65) Prior Publication Data

US 2011/0065979 A1    Mar. 17, 2011

Related U.S. Application Data

(60) Provisional application No. 61/276,589, filed on Sep. 14, 2009.

(51) Int. Cl.
*A61F 5/56* (2006.01)

(52) U.S. Cl.
USPC .......................................................... 600/27

(58) Field of Classification Search
USPC ...................................... 600/26–28; 128/848
See application file for complete search history.

(56) References Cited

U.S. PATENT DOCUMENTS

| | | | |
|---|---|---|---|
| 2003/0199945 A1* | 10/2003 | Ciulla | 607/48 |
| 2005/0043772 A1* | 2/2005 | Stahmann et al. | 607/42 |
| 2005/0085865 A1* | 4/2005 | Tehrani | 607/42 |
| 2005/0283039 A1 | 12/2005 | Cornel | |
| 2006/0145878 A1* | 7/2006 | Lehrman et al. | 340/575 |
| 2007/0150006 A1 | 6/2007 | Libbus et al. | |

FOREIGN PATENT DOCUMENTS

| WO | WO 02/100267 A1 | 12/2002 |
|---|---|---|
| WO | WO 2007/100958 A1 | 9/2007 |

OTHER PUBLICATIONS

Notification of Transmittal of the International Search Report and the Written Opinion of the International Searching Authority, or the Declaration dated Jan. 21, 2011 in connection with International Patent Application No. PCT/US2010/048798.

* cited by examiner

*Primary Examiner* — Christine Matthews
*Assistant Examiner* — Joshua D Lannu

(57) ABSTRACT

An apparatus and method for causing a conditioned reflex in a person. The apparatus includes a detector configured to detect a physiological condition of the person, the physiological condition associated with an onset of a sleep apnea event. The apparatus also includes a controller configured to transmit a stimulus to the person upon a detection of the physiological condition. The controller is also configured to determine if the physiological condition is still occurring. The controller is further configured, upon a determination that the physiological condition is still occurring, to repeat the transmitting and determining steps.

20 Claims, 4 Drawing Sheets

SYSTEM AND METHOD FOR TRAINING AND PROMOTING A CONDITIONED REFLEX INTERVENTION DURING SLEEP

CROSS-REFERENCE TO RELATED APPLICATION(S) AND CLAIM OF PRIORITY

The present application is related to U.S. Provisional Patent Application No. 61/276,589, filed Sep. 14, 2009, entitled "SYSTEM AND METHOD FOR TRAINING AND PROMOTING A CONDITIONED REFLEX INTERVENTION DURING SLEEP". Provisional Patent Application No. 61/276,589 is assigned to the assignee of the present application and is hereby incorporated by reference into the present application as if fully set forth herein. The present application hereby claims priority under 35 U.S.C. §119(e) to U.S. Provisional Patent Application No. 61/276,589.

TECHNICAL FIELD

This disclosure is generally directed to sleep disorders and more particularly to systems and methods for training and promoting a conditioned reflex intervention for treatment of obstructive sleep apnea (OSA) and other physiological conditions.

BACKGROUND

Apnea is the cessation of breathing. Sleep apnea is the cessation of breathing during sleep. Sleep apnea is a common sleep disorder that affects over twelve million (12,000,000) people in the United States. Persons with sleep apnea may stop and start breathing several times an hour while sleeping. Each individual episode of the cessation of breathing is referred to as a sleep apnea event.

When a person stops breathing during sleep the person's brain soon senses that oxygen levels in the blood are low and carbon dioxide levels in the blood are high. The brain then sends emergency signals to the body to cause the body to try to increase gas exchange in the lungs to increase the amount of oxygen and to decrease the amount of carbon dioxide. The body's autonomic physiological reflexes initiate survival reactions such as gasping for air, the production of enzymes to constrict arteries to increase blood pressure, and the production of enzymes to increase heart rate. The person will then usually gasp for air and thereby restore the effective gas exchange of oxygen and carbon dioxide in the lungs. This causes the sleep apnea event to end.

The brain may also cause the body's autonomic physiological reflexes to release large amounts of adrenaline in order to stir the person to gasp for air. Over a period of time repeated rushes of adrenaline in the body can have negative effects and can lead to heart damage and other medical problems.

Apneic events, full apneas or partial closures termed hypopneas lasting more than a few seconds also result in a drop in blood oxygen saturation. Desaturations of three percent or more occurring repeatedly during the night lead to tissue damage.

Often the person wakes up while gasping for air. Even if the person does not become conscious while gasping for air, the body's sleep state is interrupted and the body is physiologically stressed during each sleep apnea event. Sleep apnea events can occur multiple times during a period of sleep. That is, the process of ceasing to breathe, becoming physiologically stressed, and gasping for air may be repeated numerous times during a period of sleep. Successive sleep apnea events cause a person to experience many short interrupted periods of sleep. This sleep fragmentation is physiologically and psychologically harmful.

There are two forms of sleep apnea, central sleep apnea and obstructive sleep apnea. At the present time, central sleep apnea and obstructive sleep apnea are thought to originate from two different sources. Central sleep apnea appears to be linked to a malfunction of the brain that interferes with neurological signals that normally control the breathing process. Obstructive sleep apnea is caused by a blockage of the breathing airway that completely (apnea) or almost completely (hypopnea) stops the flow of air to and from the lungs. A common form of obstructive sleep apnea occurs when fleshy tissue in a sleeping person's throat collapses and seals off the pharyngeal airway. A condition called mixed sleep apnea results when central sleep apnea events and obstructive sleep apnea events alternate.

Successful treatment for obstructive sleep apnea must ensure that a person's breathing passages remain open during sleep. The simplest treatments include weight reduction, change in body position while sleeping, avoidance of alcohol, avoidance of sedatives, and similar changes in lifestyle. When anatomical obstructions are found to be the source of obstructive sleep apnea, surgery may be required for removal of enlarged tonsils, enlarged adenoids, excess tissue at the back of the throat, and similar types of obstructions. In more extreme cases, an opening may be created in the trachea in order to bypass the obstruction that is blocking the airway during sleep.

One device for the treatment of obstructive sleep apnea is a device that pumps fresh air into a mask worn over the nose. This device provides what is known as nasal continuous positive airway pressure (CPAP). When the mask and air flow are properly adjusted, the air pressure opens the upper air passage enough to prevent snoring and obstructive sleep apnea. The disadvantages of the CPAP treatment include 1) discomfort and sleep disruption caused by the nose mask and the mechanism for connecting the mask to the air pumping device, and 2) original and on-going cost for the apparatus, and 3) inconvenience when the sleeping location changes. Some newer types of CPAP devices do not use a mask (e.g., the CPAP device disclosed in U.S. Pat. No. 6,012,455).

SUMMARY

An apparatus for causing a conditioned reflex in a person is provided. The apparatus includes a detector configured to detect a physiological condition of the person, the physiological condition associated with an onset of a sleep apnea event. The apparatus also includes a controller configured to transmit a stimulus to the person upon a detection of the physiological condition. The controller is also configured to determine if the physiological condition is still occurring. The controller is further configured, upon a determination that the physiological condition is still occurring, to repeat the transmitting and determining steps.

A method for causing a conditioned reflex in a person is provided. The method includes detecting a physiological condition of the person, the physiological condition associated with an onset of a sleep apnea event. The method also includes, upon a detection of the physiological condition, transmitting a stimulus to the person. The method further includes determining if the physiological condition is still occurring. The method still further includes, upon a determination that the physiological condition is still occurring, repeating the transmitting and determining steps.

A method for training a conditioned reflex in a person is provided. The method includes transmitting a stimulus to the person, wherein the person is in preparation for sleep and the stimulus is configured to induce the person to take an action to counter a physiological condition. The method also includes waiting for a predetermined time period. The method further includes repeating the transmitting and waiting steps for a first plurality of repetitions.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of this disclosure and its features, reference is now made to the following description, taken in conjunction with the accompanying drawings, in which.

DETAILED DESCRIPTION

The present disclosure provides systems and methods for training and promoting a conditioned reflex intervention for treatment of obstructive sleep apnea (OSA) and other physiological conditions.

It is advantageous to be able to detect and terminate the onset of an obstructive sleep apnea event before the obstructive sleep apnea event fully develops and cessation of breathing occurs. Detecting and terminating the onset of an obstructive sleep apnea event before the sleeping person actually stops breathing means that the sleeping person does not have to suffer through the physiologic consequences of adrenergic response and blood oxygen desaturation.

U.S. Pat. No. 6,666,830 (hereinafter "the '830 patent") describes a system and method for detecting the onset of an obstructive sleep apnea event before the obstructive sleep apnea event fully develops and before cessation of breathing occurs. U.S. Pat. No. 6,935,335 (hereinafter "the '335 patent") describes a system and method for terminating a physiological process that causes a sleep apnea event before cessation of breathing occurs. The '830 and '335 patents are incorporated herein by reference.

A conditioned reflex intervention system of the present disclosure employs a device that senses acoustic changes associated with early airflow limitation and other breathing-related sounds, such as snoring. The device uses miniature microphones embedded in a soft, pliant collar worn around the neck that capture the breath sound power spectrum.

The conditioned reflex intervention system of the present disclosure may be a stand-alone device, or may be made a part of the other systems. For example, it could be made a module of a head and jaw extension reflex system, also disclosed herein.

Figure 1:
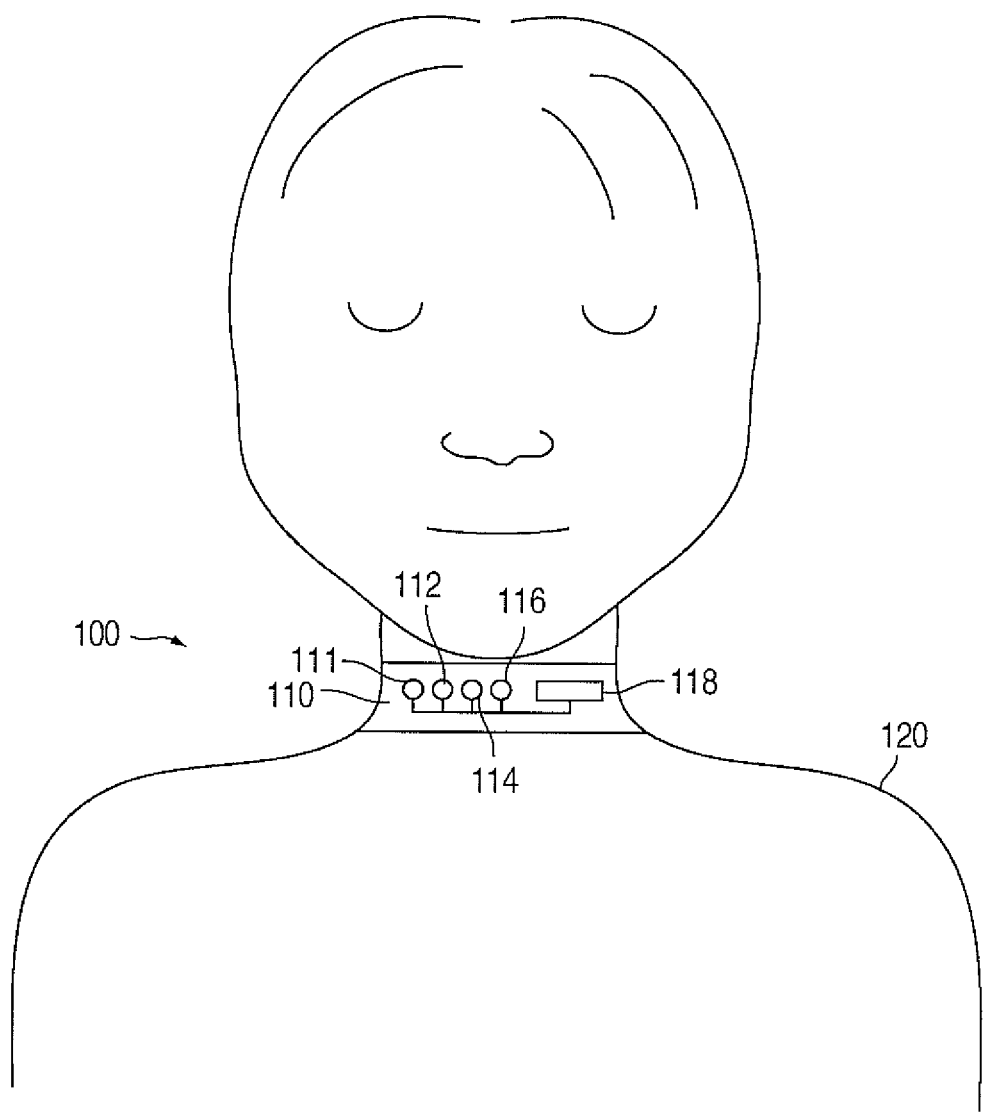
FIG. 1 depicts a device for training and promoting a conditioned reflex intervention for treatment of obstructive sleep apnea (OSA) and other physiological conditions, according to one embodiment of the present disclosure.

FIG. 1 depicts a device for training and promoting a conditioned reflex intervention for treatment of obstructive sleep apnea (OSA) and other physiological conditions, according to one embodiment of the present disclosure.

Device 100 includes a soft, pliant collar 110 that is worn around the neck of a patient 120. The collar 110 includes one or more microphones 111, a microcontroller 112, a miniature voice synthesizer 114, a battery 116, and an on/off/volume control switch 118. When the one or more microphones 111 detect acoustic changes associated with the advent of an apneic or hypopneic event or other physiological condition, the microcontroller 112 will instruct the voice synthesizer 114 to issue a whispered cue or other stimulus. The patient is trained to react to the cue by initiating a movement of one or more parts of the body, such as head and jaw movements that restore and maintain upper airway patency. Over time, these actions can be trained by the device to become a subconscious reflex.

Swallow Reflex

One particularly beneficial use of the conditioned reflex intervention method of the present disclosure is to clear an OSA event through the swallow reflex.

There are three stages to the swallow—oral, pharyngeal, and esophageal. The last two are autonomic, but the oral stage is under voluntary neuro-muscular control, though it is often initiated with little conscious thought. To the benefit of an OSA patient, quasi-autonomous reflexes are easy to condition.

In the oral bolus transport sub-stage, once the tongue has made contact with the soft palate, the veli palatini, levator velipatini, and the palatophayrngeus muscles contract. Their action draws the velum superiorly and posteriorly opening the nasopharynx to permit passage of the bolus. Almost simultaneously, the hyomandibular complex retracts away from the posterior pharyngeal wall assuring a patent lumen for the traverse of whatever is esophagus bound.

Once can feel this action by placing the thumb and forefinger on the neck just below the mandible and above the cricoid cartilage at the 70 degree and 290 degree positions. By swallowing, the oropharynx lift will be felt.

The initiation of a swallow will break the mucus mediated oropharyngeal seal that precipitates the advent of an OSA event. It is possible to condition a swallow reflex in many patients that suffer from OSA if they participate in the simple training program described herein.

In certain embodiments, the swallow reflex may also act to inhibit snoring of the patient. The swallow reflex inhibits snoring because the act of swallowing involves elevating the soft palate against the posterior wall of the nasopharynx. That act stops the soft palate from flapping during the act of the swallow. A snore is the flapping of the soft palate into the lumen of the nasopharynx.

Using existing sound classification logic found in the OSA detection system of patents '335 and '830, it is possible to recognize a snoring sound. When the snore is recognized, the conditioned reflex methods of the present disclosure use the voice synthesizer to cue a swallow. However, the swallow is often only a short-lived intervention, with the snore pattern returning quickly. Therefore, in certain embodiments, it is desirable to condition a second reflex that initiates a change in body position because most snoring occurs when the patient is supine (i.e., lying on his or her back). This turning reflex may be a response to an audible stimulus, such as a voice synthesizer whispering to the patient to "turn".

Figure 2:
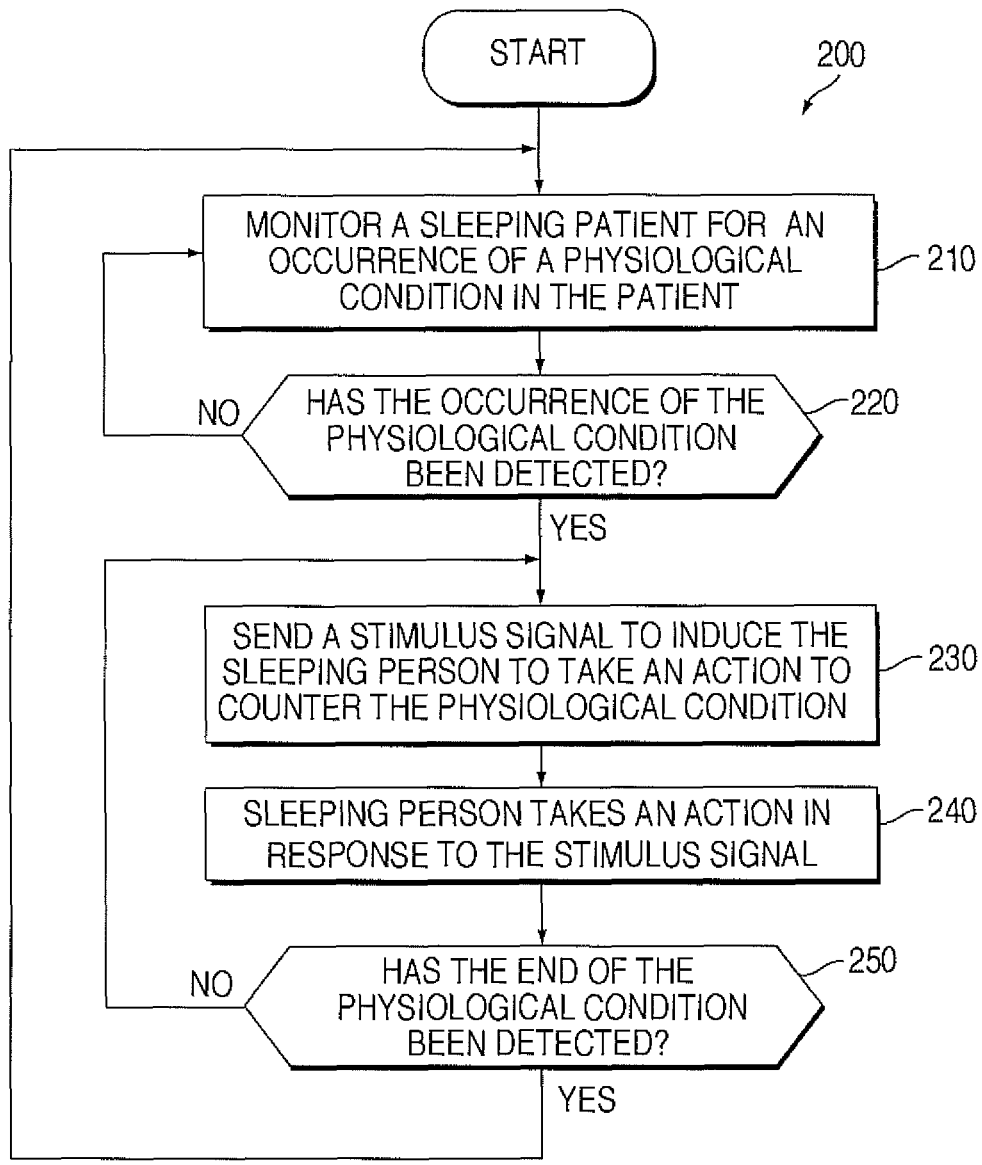
FIG. 2 depicts a method for using a conditioned reflex to counter a physiological condition in a sleeping patient, according to one embodiment of the present disclosure.

FIG. 2 depicts a method 200 for using a conditioned reflex to counter a physiological condition in a sleeping patient, according to one embodiment of the present disclosure. In certain embodiments, the physiological condition may be the onset of an OSA event and the conditioned reflex may be swallowing. In other embodiments, the physiological condition may be one or more other conditions, such as high blood pressure, rapid heart rate, rapid breathing, snoring, etc. Such other physiological conditions may be associated with other conditioned reflexes.

First, a detection device monitors a sleeping patient for an occurrence of a physiological condition in the patient (step 210). In certain embodiments, the detection device is a therapeutic collar worn around the throat of the patient, such as the collar 110. Next, the detection device detects if the patient is experiencing an occurrence of the physiological condition (step 220). If an occurrence of the physiological condition has not been detected, then the method returns to step 210.

On the other hand, if an occurrence of the physiological condition has been detected, then a stimulus signal is activated to induce the sleeping patient to take an action to counter the physiological condition (step 230). In certain embodiments, the stimulus signal may be a whispered cue to "swallow". In other embodiments, the whispered cue may be another message, such as "relax", "breathe slowly", "turn over", etc. In still other embodiments, the stimulus signal may be a tone, vibration, or other non-verbal signal.

Another example of a non-verbal stimulus is an aroma. Typically, the nose is still active while a person sleeps. Thus, certain patients might find olfactory stimulation effective. For such patients, the stimulus may be a release of an aroma in the vicinity of the patient's nose.

Next, the sleeping patient responds to the stimulus signal by taking an action (step 240). The action taken by the sleeping patient depends on the stimulus signal that is activated. For example, in certain embodiments, if the stimulus signal is a whispered cue "swallow", then the patient responds by swallowing. If the stimulus signal is a whispered cue "turn over", then the patient turns over in bed. In certain embodiments, if the stimulus signal is a vibration, then the patient responds by taking an action associated with a vibration stimulus. In still other embodiments, the patient may respond to an aroma stimulus. The action taken by the sleeping patient in response to a stimulus is trained according to the training method described in the present disclosure.

Next, the detection device determines if the patient is still experiencing the physiological condition, or if the physiological condition has ended (step 250). If the patient is still experiencing the physiological condition, the method returns to step 230 in order to send another stimulus signal. On the other hand, if the end of the physiological condition has been detected, then the method returns to step 210 to continue monitoring the patient for another occurrence of the physiological condition.

Throat Clearing

The process of drawing in breath results in negative pressures that would cause collapse of the pharyngeal airway if they were unopposed. Two sets of muscles located on opposite sides of the pharynx, the geniohyoid and sternohyoid, collectively known as the pharyngeal dilator muscles, oppose such collapse.

Passive mechanical and active neuromuscular influences contribute to the patency and collapsibility of the pharyngeal dilator muscles. During waking hours, patency is maintained by the autonomous nervous system but increases in the tone of the pharyngeal dilator muscles are subject to volition (conscious control) such as when an individual "clears his throat."

During sleep, with the advent of a general reduction in muscle tone throughout the body, hypo-tonality may occur in the pharyngeal dilator muscles and they may relax into close proximity creating an obstructive apneic event, an occurrence that is facilitated by the mucus film that coats the epithelia of the respiratory passages.

Mucus is a viscous secretion that serves as a diffusion barrier against noxious substances throughout the hollow organs of the body. In the pharynx it also serves as a lubricant to minimize airway sheer stresses. For example, coughs can generate air blasts with velocities over one hundred miles per hour, resulting in possible sheer stresses.

The energetics of sticky thin films such as mucus promote adhesion of opposing tissues so that during sleep the hypo-tonality of the pharyngeal dilator muscles promotes a series of obstructive apneic events which are broken when the sympathetic nervous system, reacting to the imbalance of oxygen and carbon dioxide in the blood stream, launches an adrenergic response.

Mucus is in copious supply in the respiratory tract and the body has an organized set of clearing and scavenging reflexes. The cough and the sneeze are examples of reflexes whose source is propulsive movement of the diaphragm. There is difference in their neural control, however. Coughs are usually under autonomous neural control, but can be instigated by volition. The initiation of the sneeze, on the other hand, is not subject to volition.

The clearing of the accumulation of mucus in the pharynx can be autonomic, but generally is under volition even though most clearing activity does not intrude into consciousness the way that sneezes and coughs do.

The process of clearing mucus from the pharynx during wakefulness is not needed to prevent the occurrence of a mucus mediated adhesion of pharyngeal tissue because there is sufficient tone in the pharyngeal dilator muscles to prevent collapse of the airway. However, during sleep, when the pharyngeal dilator muscles have lost their tone, activation of the mucus clearing reflex can restore patency because the reflex requires the restoration of tone to the pharyngeal dilator muscles.

Using the systems and methods of the present disclosure, such as method 200, patients can be trained to initiate the throat clearing maneuver when they are given a cue from the intervention package. As described with respect to method 200, the cue may be a whispered word, or possibly a low level sound, a gentle vibration, an aroma, or another suitable stimulus. The throat clearing reflex through auto-suggestion can be used as a means of preempting the adrenergic reflex by breaking the adhesive seal mediated by the mucus of the pharynx.

In certain embodiments, a mucus/airway scavenging reflex might be combined with a swallow reflex. Mucus/airway scavenging is a bit more complex than swallowing. A different set of muscles initially are employed in scavenging. Therefore, the scavenging reflex may be stimulated first, and then followed by the swallow reflex.

Head Extension/Mandible Projection

One method of intervention according to the present disclosure includes detecting the advent of a narrowing of the upper airway, and then conditioning the subconscious mind to initiate a movement of the head and jaw that averts upper airway narrowing or collapse upon activation of a stimulus. In certain embodiments, the conditioned reflex method 200 may be used to initiate the head and jaw extension. The conditioning of the subconscious movement reflex can be achieved through auto-suggestion training techniques implemented at bedtime, such as the training method described herein.

In certain embodiments, it is advantageous to have a conditioned reflex that will project the mandible (the lower jaw bone) forward when an OSA event is anticipated. As the mandible advances it carries the tongue forward with it thus breaking the seal that develops when the base of the tongue makes contact with the posterior surface of the oropharynx, a full obstructive event. Projecting the mandible forward will also avert hypopnea, a partial obstruction (or narrowing) of the oropharynx that restricts the passage of breath sufficient to result in blood oxygen desaturation.

In certain embodiments, this action might be trained in isolation. In other embodiments, it may be beneficial to couple the conditioned reflex action of the forward mandible thrust with a conditioned reflex action of the neck extension. For some patients, this is likely to be the preferred implementation for intervention in sleep-disturbed breathing.

Use of Stimulus During REM Sleep

The system and method described in the '335 patent employs a stimulus generator that creates a low intensity stimulus signal when the system detects the onset of a sleep apnea event. The intensity of the stimulus signal is low so that the sleeping person does not wake up when the stimulus signal is activated.

The sleeping person subconsciously perceives the activation of the low intensity stimulus signal. In some embodiments, the person may be trained to subconsciously respond to the occurrence of the stimulus signal by inclining his or her head backwards, or moving one or more parts of the body in some manner.

This approach may not work during a sleep state known as "rapid eye movement" sleep or "REM sleep". REM sleep is characterized by dreaming and rapid eye movement. On the average, REM sleep occurs during about seventeen percent (17%) of sleep time for men and during about eighteen percent (18%) of sleep time for women. See "The Occurrence of Sleep-Disordered Breathing Among Middle-Aged Adults," New England Journal of Medicine, 1993.

During the dream stage of REM sleep, the brain places the voluntary skeletal muscles of the body into a state of paralysis in order to prevent the movement of the sleeping person's limbs. This naturally induced paralysis prevents the sleeping person from moving his or her limbs in reaction to the content of a dream. Thus, in REM sleep, the method described in the '335 patent may not work because the voluntary skeletal muscles in the neck are paralyzed. The paralysis is controlled by centers in the brain that inhibit the conduction of a movement command from the brain down the efferent neuromuscular nerves. Nevertheless, the skeletal muscles will contract in response to direct electrical stimulation. Thus, using the system and method disclosed herein, it is possible to intervene in an incipient OSA event even during REM sleep.

There are many methods for detecting REM sleep. Brain electrical activity can be measured using electrocephalography; eye movements can be measured by using electrooculography; and muscle hypotonia can be measured by using electromyography. The sensors for these devices are electrodes placed on the head, close to the eyes, or on the jaw. To detect REM sleep, the electromyography electrodes are usually applied to the jaw because in REM sleep the jaw goes completely slack.

In certain embodiments, when the detection system detects REM sleep, an OSA intervention system will enable electrodes that will directly stimulate the skeletal muscles on the back of the neck to avert the adrenergic response when an incipient OSA event is detected. In advantageous embodiments, the OSA intervention system will use jaw electromyography because the sensing electrode is just a few centimeters from the collar which houses the other components of the system. The system will revert to using a conditioned reflex (e.g., the conditioned reflex method 200), and will disable the direct stimulation process once the sleeper returns to non-REM sleep.

It is noted that, by using the swallow reflex, a patient does not encounter the problem of the voluntary muscles being paralyzed during REM sleep because the swallow reflex is active during REM sleep. Thus, a conditioned swallow reflex will operate during REM sleep, and will also produce minimal, if any, arousal.

Figure 3:
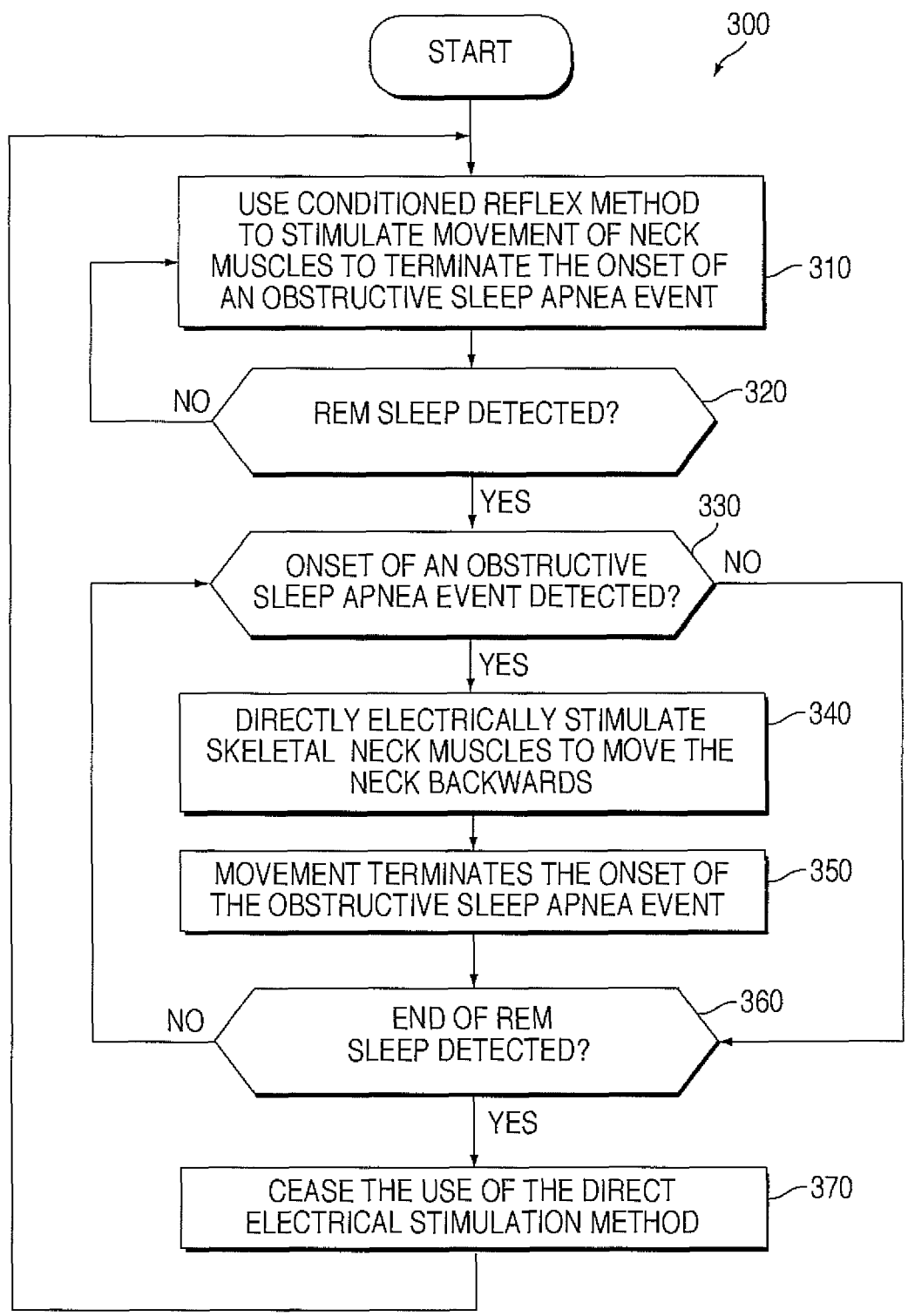
FIG. 3 depicts a method for averting an OSA event during REM sleep using an electrical stimulus, according to one embodiment of the present disclosure.

FIG. 3 depicts a method for averting an OSA event during REM sleep using an electrical stimulus, according to one embodiment of the present disclosure. Method 300 starts by using a conditioned reflex method to stimulate movement of the neck muscles in case of an OSA event during non-REM sleep (step 310). In certain embodiments, step 310 may include the conditioned reflex method 200, as described in FIG. 2.

Next, a REM sleep detection device determines if the sleeping patient is in a state of REM sleep (step 320). If the sleeping patient is not in a state of REM sleep, the method returns to step 310. If the patient is in a state of REM sleep, then a detection device will determine if the patient is experiencing the onset of an OSA event (step 330). If the patient is not experiencing the onset of an OSA event, then the method moves to step 360, discussed below.

On the other hand, if the patient is experiencing the onset of an OSA event, then electrodes attached to the patient's neck electrically stimulate the neck muscles to move the neck backwards (step 340). This movement helps to open the airway, thus terminating the onset of the OSA event (step 350).

Next, the REM sleep detection device determines if the sleeping patient is still in a state of REM sleep, or if the end of REM sleep has occurred (step 360). If the end of REM sleep is not detected by the REM sleep detection device, then the method returns to step 330.

On the other hand, if the end of REM sleep is detected, then neck muscles are no longer in a state of paralysis, and it is no longer necessary to use electrical stimulation to move the neck muscles (step 370). Accordingly, the method returns to the conditioned reflex method described in step 310. The method 300 may continue until the patient awakens.

Training

In the intervention of OSA events, conditioned reflexes (e.g., extension of the head upward, turning over, slowed breathing, etc.) are triggered by a stimulus, such as a sound, a vibration, a whispered cue, or an aroma. These triggering actions are commanded when the onset of an OSA event is sensed by the method described in the detection patent. The present disclosure provides a training system that conditions a subconscious reflex while the subject is falling asleep.

Training may be achieved by using a suggestion. In one embodiment, a therapeutic collar will incorporate means that sense that a physiological condition (e.g., an obstruction of the pharynx) is imminent. When commanded by the logic in the device, a voice synthesizer will whisper the suggestion "swallow". To ingrain the appropriate reaction in the patient to the suggestion "swallow", the therapeutic collar will have a "training" mode that is initially entered every time the therapeutic collar is switched on.

In the training mode, immediately after the patient positions the therapeutic collar around his or her throat, and as the patient prepares for sleep, the voice synthesizer will repeat at some settable repetition rate and for a settable duration of time, the suggestion "swallow". Every time the patient hears the suggestion "swallow", he or she will be expected to swallow.

The cueing of the suggestion "swallow" will continue for a settable period of time which is longer than the duration of the patient's pre-sleep latency. At the point that the patient is presumed to be sleeping the training mode will switch to the surveillance mode. In the surveillance mode, the suggestion "swallow" will only be cued when an incipient obstruction is sensed.

In certain embodiments, to ensure that the suggestion "swallow" is kept ingrained, the therapeutic collar is configured to always first enter the training mode before it switches to the surveillance mode. This constant training will ensure that the swallow reflex will be reliably conditioned at the cue "swallow". To train the intervention reflex as a subconscious reaction to the cue during the home adaptation training stage, the training time may be divided into time brackets as follows:

First bracket (the subject going to bed turns off light and activates the device on switch): Bracket lasts two elapsed minutes. There is a cue every twenty seconds. Patient presses log button and executes intervention maneuver.

Second bracket: Bracket lasts two minutes. There is a cue every thirty seconds. Patient presses log button and executes intervention maneuver.

Third bracket: Bracket lasts six minutes. There is a cue every minute. Patient presses log button and executes intervention maneuver.

Fourth bracket: Bracket lasts ten minutes. There is a cue every two minutes. Patient presses log button and executes intervention maneuver, if awake.

Fifth bracket: Continuing through the night. There is cue every five minutes. Patient presses log button and executes intervention maneuver, if awake.

In some environments, patients that are receptive to auto-suggestion will be trained after three weeks. In other environments, training may take four weeks or longer.

It is understood that the specific values and times described herein are for example purposes; other values may be possible or desirable. In certain embodiments, it may be necessary to continually reinforce the conditioned reflex established by auto-suggestion. Therefore, upon start-up before each sleep period, the device will re-enter the training mode for twenty to thirty minutes. It will then enter a normal operating mode where it will issue cues only when a potential obstructive event is anticipated because of changes in breath spectral power.

In certain embodiments, the conditioned reflex is trained or reinforced by the use of electrodes that stimulate muscle contractions. For example, in order to train the head to tilt backward in response to an audible stimulus, electrodes are used to cause contractions of the muscles of the back of the neck. Such a method may be needed for OSA patients. Once the conditioned reflex is established, it is no longer necessary to use electrodes to effect contraction of the skeletal muscles of the neck.

The training method disclosed herein may be used for physiological conditions other than OSA. For example, snoring, fast breathing, high blood pressure or heart rate, etc., may be relieved by a conditioned reflex that is learned through the disclosed training method. Different stimuli may be used to provoke different conditioned reflexes.

Figure 4:
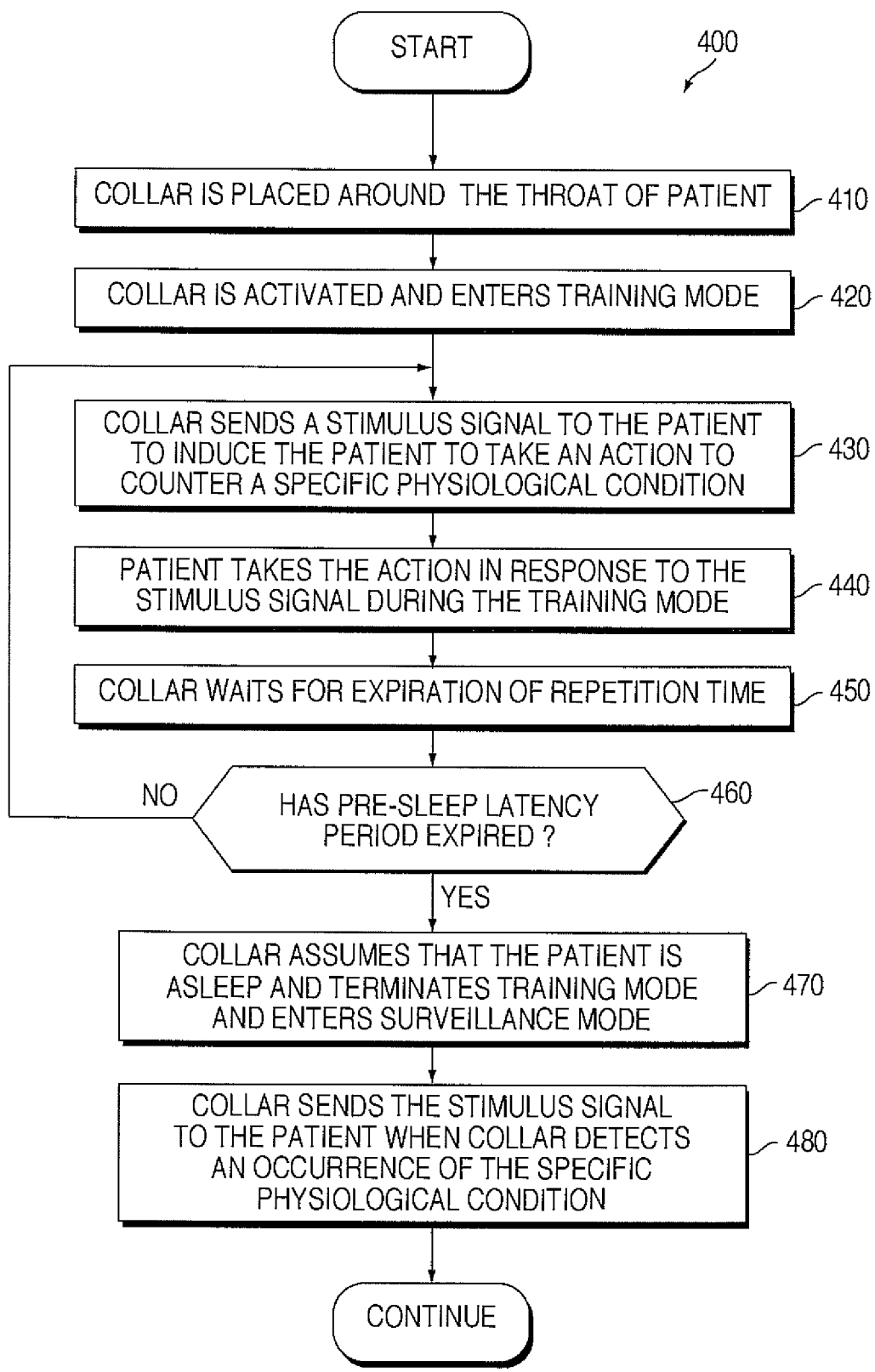
FIG. 4 depicts a method for training a conditioned reflex in a sleeping patient in order to counter a specific physiological condition, according to one embodiment of the present disclosure.

FIG. 4 depicts a method 400 for training a conditioned reflex in a sleeping patient in order to counter a specific physiological condition, according to one embodiment of the present disclosure. In certain embodiments, the physiological condition may be the onset of an OSA event and the conditioned reflex may be swallowing. In other embodiments, the physiological condition may be one or more other conditions, such as high blood pressure, rapid heart rate, rapid breathing, snoring, etc. Such other physiological conditions would be associated with other conditioned reflexes.

First, a therapeutic collar is placed around the throat of the patient (step 410). Next, the collar is activated and is initially placed in the training mode (step 420). Next, as the patient prepares for sleep, a stimulus signal is sent to the patient (step 430). In certain embodiments, the stimulus may be a voice synthesizer on the collar whispering the word "swallow" to the patient. In other embodiments, the stimulus may be another whispered word or phrase, such as "relax" or "breathe slowly". Next, the patient takes an action in response to the stimulus signal (step 440). For example, in response to hearing the word "swallow", the patient may swallow. As another example, in response to hearing the phrase "breathe slowly", the patient may slow his or her breathing.

The training mode requires a repetitive series of steps, and there is typically a delay between repetitions. Accordingly, the collar waits for the expiration of the repetition time (step 450). At the expiration of the repetition time, it is determined whether the patient's pre-sleep latency period has expired (step 460). If the period has not yet expired, the method 400 returns to step 430 for another repetition of steps. On the other hand, if the patient's pre-sleep latency period has expired, then the patient is presumed to be sleeping, and the collar terminates training mode and switches to surveillance mode (step 470).

During surveillance mode, the collar (or other monitoring device) monitors the patient for signs that indicate a specific physiological condition, (e.g., the onset of an OSA event). If the specific physiological condition is detected, the collar sends the stimulus signal (e.g., a whispered "swallow") to the patient (step 480). The stimulus signal causes the patient to perform the conditioned action (e.g., the patient swallows), thus relieving the physiological condition. In certain embodiments, the surveillance mode may continue as long as the patient is asleep. In certain embodiments, the surveillance mode may incorporate the conditioned reflex method 200 as described in FIG. 2.

It may be advantageous to set forth definitions of certain words and phrases used throughout this patent document. The term "couple" and its derivatives refer to any direct or indirect communication between two or more elements, whether or not those elements are in physical contact with one another. The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. The term "controller" means any device, system, or part thereof that controls at least one operation. A controller may be implemented in hardware, firmware, software, or some combination of at least two of the same. The functionality associated with any particular controller may be centralized or distributed, whether locally or remotely.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. An apparatus for causing a conditioned reflex in a person, the apparatus comprising:
    a power source configured to supply power to the apparatus;
    a detector configured to detect a physiological condition of the person, the physiological condition associated with an onset of a sleep apnea event; and
    a controller configured to:
    transmit a stimulus to the person upon a detection of the physiological condition, the stimulus configured to induce the person to perform at least two actions to counter the physiological condition, wherein a first of the at least two actions comprises turning over and a second of the at least two actions comprises swallowing or clearing a throat;
    determine if the physiological condition is still occurring; and
    upon a determination that the physiological condition is still occurring, repeat the transmitting and determining steps.

2. The apparatus as set forth in claim 1, wherein the second of the at least two actions comprises swallowing.

3. The apparatus as set forth in claim 1, wherein the second of the at least two actions comprises clearing a throat.

4. The apparatus as set forth in claim 1, wherein the controller is configured to monitor the person while the person is asleep.

5. The apparatus as set forth in claim 1, wherein the physiological condition is a snore.

6. The apparatus as set forth in claim 1, wherein the stimulus is selected from a plurality of predetermined stimuli, each predetermined stimulus associated with a predetermined physiological condition, the stimulus selected based on the detected physiological condition.

7. The apparatus as set forth in claim 1, wherein the stimulus is a whispered cue from a voice synthesizer.

8. The apparatus as set forth in claim 1, wherein:
    the controller is configured to detect that the person is in a state of REM (rapid eye movement) sleep; and
    the stimulus transmitted to the person is an electrical stimulus configured to cause neck muscles in the person to move a neck of the person backwards.

9. A method for causing a conditioned reflex in a person, the method comprising:
    detecting, by a microphone, a physiological condition of the person, the physiological condition associated with an onset of a sleep apnea event;
    upon a detection of the physiological condition, transmitting a stimulus to the person, the stimulus configured to induce the person to perform at least two actions to counter the physiological condition, wherein a first of the at least two actions comprises turning over and a second of the at least two actions comprises swallowing or clearing a throat;
    determining if the physiological condition is still occurring; and
    upon a determination that the physiological condition is still occurring, repeating the transmitting and determining steps.

10. The method as set forth in claim 9, wherein the second of the at least two actions comprises swallowing.

11. The method as set forth in claim 9, wherein the second of the at least two actions comprises clearing a throat.

12. The method as set forth in claim 9, further comprising monitoring the person while the person is asleep.

13. The method as set forth in claim 9, wherein the physiological condition is a snore.

14. The method as set forth in claim 9, wherein the stimulus is selected from a plurality of predetermined stimuli, each predetermined stimulus associated with a predetermined physiological condition, the stimulus selected based on the detected physiological condition.

15. The method as set forth in claim 9, wherein the stimulus is a whispered cue from a voice synthesizer.

16. The method as set forth in claim 9, further comprising detecting that the person is in a state of REM (rapid eye movement) sleep, wherein the stimulus transmitted to the person is an electrical stimulus configured to cause neck muscles in the person to move a neck of the person backwards.

17. A method for training a conditioned reflex in a person, the method comprising:
    transmitting, by a device worn around the person's neck, a stimulus to the person, wherein the person is in preparation for sleep and the stimulus is configured to induce the person to perform at least two actions to counter a physiological condition, wherein a first of the at least two actions comprises turning over and a second of the at least two actions comprises swallowing or clearing a throat;
    waiting for a predetermined time period; and
    repeating the transmitting and waiting steps for a first plurality of repetitions.

18. The method as set forth in claim 17, wherein the stimulus is one of: a whispered cue from a voice synthesizer and an aroma.

19. The method as set forth in claim 17, wherein the second of the at least two actions comprises clearing a throat.

20. The method as set forth in claim 17, further comprising repeating the transmitting and waiting steps for a second plurality of repetitions, wherein the waiting time period for the second plurality of repetitions is longer than the waiting time period for the first plurality of repetitions.

* * * * *